United States Patent
Frascini et al.

(10) Patent No.: US 9,757,405 B2
(45) Date of Patent: Sep. 12, 2017

(54) COMPOSITIONS COMPRISING RUTIN USEFUL FOR THE TREATMENT OF TUMORS RESISTANT TO CHEMOTHERAPY

(71) Applicant: PROBIOTICAL S.P.A., Novara (IT)

(72) Inventors: Franco Frascini, Novara (IT); Marcello Iriti, Novara (IT); Paolo Maestri, Novara (IT); Lia Rimondini, Novara (IT); Enrico Catalano, Novara (IT); Saverio Megna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

(21) Appl. No.: 14/917,939

(22) PCT Filed: Jul. 17, 2014

(86) PCT No.: PCT/IB2014/063187
§ 371 (c)(1),
(2) Date: Mar. 9, 2016

(87) PCT Pub. No.: WO2015/036875
PCT Pub. Date: Mar. 19, 2015

(65) Prior Publication Data
US 2016/0213698 A1 Jul. 28, 2016

(30) Foreign Application Priority Data
Sep. 10, 2013 (IT) .............................. MI2013A1495

(51) Int. Cl.
| | | |
|---|---|---|
| A01N 43/04 | (2006.01) |
| A61K 31/70 | (2006.01) |
| A61K 31/7048 | (2006.01) |
| A61K 31/136 | (2006.01) |
| A61K 31/337 | (2006.01) |
| A61K 31/34 | (2006.01) |
| A61K 31/365 | (2006.01) |
| A61K 31/4375 | (2006.01) |
| A61K 31/4741 | (2006.01) |
| A61K 31/513 | (2006.01) |
| A61K 31/519 | (2006.01) |
| A61K 31/555 | (2006.01) |
| A61K 31/675 | (2006.01) |
| A61K 31/704 | (2006.01) |
| A61K 36/28 | (2006.01) |
| A61K 36/29 | (2006.01) |
| A61K 36/66 | (2006.01) |
| A61K 45/06 | (2006.01) |
| A61K 31/4745 | (2006.01) |
| A61K 31/664 | (2006.01) |

(52) U.S. Cl.
CPC ........ *A61K 31/7048* (2013.01); *A61K 31/136* (2013.01); *A61K 31/337* (2013.01); *A61K 31/34* (2013.01); *A61K 31/365* (2013.01); *A61K 31/4375* (2013.01); *A61K 31/4741* (2013.01); *A61K 31/4745* (2013.01); *A61K 31/513* (2013.01); *A61K 31/519* (2013.01); *A61K 31/555* (2013.01); *A61K 31/664* (2013.01); *A61K 31/675* (2013.01); *A61K 31/704* (2013.01); *A61K 36/28* (2013.01); *A61K 36/29* (2013.01); *A61K 36/66* (2013.01); *A61K 45/06* (2013.01)

(58) Field of Classification Search
None
See application file for complete search history.

(56) References Cited

U.S. PATENT DOCUMENTS

2013/0045179 A1  2/2013  Ciustea et al.

FOREIGN PATENT DOCUMENTS

| | | |
|---|---|---|
| CN | 1470513 A | 1/2004 |
| CN | 1560265 A | 1/2005 |
| CN | 1911951 A | 2/2007 |
| EP | 2119434 A1 | 11/2009 |
| WO | 01/78783 A2 | 10/2001 |
| WO | 2006/032380 A1 | 3/2006 |

OTHER PUBLICATIONS

Webster et al. Cancer Letters (1996), vol. 109, pp. 185-191.*
Awale et al. Cancer Res (2006), vol. 66, pp. 1751-1757.*
Hirose et al. Cancer Letters (2000), vol. 155, pp. 79-88.*
Jantova et al. Toxicology in Vitro (2007), vol. 21, pp. 25-31.*
Wang et al. Molecular Cancer (vol. 8), p. 81.*
Ahmad et al. Clinical Cancer Research (2000), vol. 6, pp. 1524-1528.*
Malikova et al. Cell Biol Toxicol (2006), vol. 22, pp. 439-453.*
International Search Report and Written Opinion for International Application No. PCT/IB2014/063187 filed Jul. 17, 2014 on behalf of Probiotical S.P.A. dated Dec. 18, 2014.
Fojo et al. "Mechanisms of Resistance to PARP Inhibitors—Three and Counting" Cancer Discovery 3(1); Jan. 2013; pp. 20-23.
Navarro-Nunez et al. "Apigenin Inhibits Platelet Adhesion and Thrombus Formation and Synergizes with Aspirin in the Suppression of the Arachidonic Acid Pathway" Journal of Agricultural and Food Chemistry; 2008; 8 pages.
Guardia et al. "Anti-inflammatory properties of plant flavonoids. Effects of rutin, quercetin and hesperidin on adjuvant arthritis in rat" Il Farmaco; vol. 56; 2001; pp. 683-687.
Metodiewa et al. "Evidence for Antiradical and Antioxidant Properties fo Four Biologically Active N,N-Diethylaminoethyl Ethers of Havanone Oximes: A Comparison with Natural Potyphenolic Havonoid (Rutin) Action" Biochemistry and Molecular Biology International; vol. 41; No. 5; Apr. 1997; pp. 1067-1075.
Luo et al. "Inhibition of Cell Growth and VEGF Expression in Ovarian Cancer Cells by Flavonoids " Nutrition and Cancer; vol. 60; No. 6; 2008; pp. 800-809.
Bourogga et al. "Hammada scoparia flavonoids and rutin kill adherent and chemoresistance leukemic cells" Leukemia Research; vol. 35; 2011; pp. 1093-1101.

(Continued)

*Primary Examiner* — Patrick Lewis
(74) *Attorney, Agent, or Firm* — Steinfl + Bruno LLP

(57) ABSTRACT

Use of rutin for increasing the effectiveness of chemotherapeutic treatments used in human and veterinary medicine for the treatment of tumors is described, in particular in case of resistance to chemotherapeutics currently in use.

8 Claims, No Drawings

(56) References Cited

OTHER PUBLICATIONS

Hanachi et al. "Cytotoxic Effect of Berberis vulgaris Fruit Extract on the Proliferation of Human Liver Cancer Cell Line (HepG2) and its Antioxidant Properties" International Journal of Cancer Research; vol. 2; No. 1; 2006; pp. 1-9.

Mani et al. "Insilico Analysis On The Effect Of Rutin Bioflayonoid And Chemotherapeutic Drug Cyclophosphamide On Nuclear Factor Kappa-B Protein Expression" International Journal of Pharma and Bio Sciences. vol. 5; No. 1; Jan. 2014; pp. 560-569.

* cited by examiner

COMPOSITIONS COMPRISING RUTIN USEFUL FOR THE TREATMENT OF TUMORS RESISTANT TO CHEMOTHERAPY

CROSS REFERENCE TO RELATED APPLICATIONS

The present application is the US national stage entry of International Patent Application No. PCT/IB2014/063187 filed internationally on Jul. 17, 2014, which claims priority to Italian Patent Application No. MI2013A001495 filed on Sep. 10, 2013.

SUMMARY OF THE INVENTION

The present invention relates to the use of rutin for increasing the effectiveness of chemotherapeutic treatments used in human and veterinary medicine for the treatment of tumors, in particular in case of resistance to chemotherapeutics currently in use.

TECHNICAL BACKGROUND

Currently, the resistance of tumor cells to chemotherapeutic treatment represents a huge problem subject to a continuous development. Drug resistance arises both in solid tumors and in lymphatic system tumors and can occur since the onset of a treatment or afterwards, after an initial positive response to the treatment. For instance, chemoresistance very often arises in the course of the treatment of tumor recurrences. An even more serious problem is represented by multiple chemoresistance, i.e. the occurrence, after a treatment with a given chemotherapeutic agent, to other chemotherapeutics.

The most reliable hypotheses about the origin of chemoresistance, which arises in most tumors initially responding to chemotherapeutic treatment, suggest that drug resistance results from a series of tumor cell mutation, from the ability of tumor cells to "learn" how to metabolize chemotherapeutics, to repair chemotherapeutic-induced damage in DNA, and to prevent chemotherapeutic-induced apoptosis.

An approach aiming at overcoming the problem of chemoresistance is the combination therapy with different types of chemotherapeutics: however, also in this case the outcomes are not satisfactory and lead to an alarmingly, increasingly frequent multiple resistance to various chemotherapeutics.

Despite the continuous research and development of new drugs, to be used also in combination, the problem of chemoresistance remains and seems to be unavoidable due to the malleable nature of cancer cells [Fojo T. and Bates S., *Cancer Discov;* 3(1); 20-3, 2012].

Therefore, there is a very strong need to overcome this problem.

Rutin, whose chemical name is 2-(3,4-dihydroxyphenyl)-4.5-dihydroxy-3-{3,4,5-trihydroxy-6-[(3,4,5-trihydroxy-6-methyloxan-2-yl)oxymethyl}oxan-2-yl]oxy-cromen-7-one, is a flavonoid glycoside consisting of aglycone quercetin (a flavonol) linked to disaccharide rutinose.

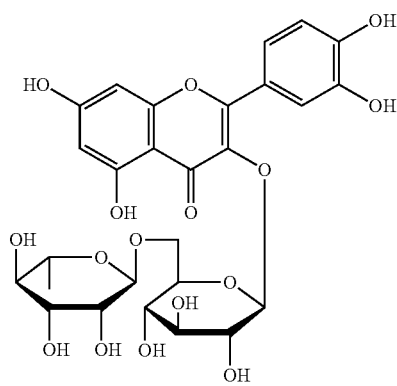

Rutin naturally occurs in many vegetables, in particular in the plants of the genus *Citrus* (citrus fruits) and *Rheum* (rhubarb), in buckwheat, in red wine, in asparagus, in peppermint, in eucalyptus, in many berries such as cranberry (*Vaccinium macrocarpon*), and mulberry.

The reinforcing effect of rutin on capillary walls and more generally its beneficial action on microcirculation are exploited in the treatment of hemorrhoids and hematomas.

Recent studies have pointed out the pharmacological properties of rutin, in particular its antiaggregating activity on platelets [Navarro-Núñez et al. (2008); *J. Agric. Food Chem.* 56 (9): 2970-6]; its anti-inflammatory activity [Guardia et al. (2001); *Il Farmaco* 56 (9): 683-7; Chan Hun Jung et al. (2007); *Arch. Pharmacal Research* 30 (12): 1599-1607]; and its anti-oxidant activity [Metodiewa et al. (1997); *IUBMB Life* 41 (5); 1067].

In-vitro studies have shown that rutin is able to inhibit the vascular endothelial growth factor, thus acting as an inhibitor of angiogenesis [Luo et al. (2008); *Nutrition and Cancer* 60 (6); 800-9].

Recently, Boutogaa et al. [*Leukemia Research* 35(2011) 1093-1101] have described how an extract of *Hammada scoparia*, containing rutin, is able to induce apoptosis in adhering leukemia cells. EP 2 119 434 describes the use of rutin in the treatment of acute myeloid leukemia, for preventing neoplastic recurrence and/or for preventing the occurrence of solid metastases. There is no mention of the effects of rutin on chemotherapeutic-resistant tumor cells.

WO 200178783 describes anti-tumor compositions comprising quercetin and many extracts of medicinal plants, but no mention is made on the activity towards chemoresistant cells.

DISCLOSURE OF THE INVENTION

The present invention relates to the use of rutin as an adjuvant for chemotherapeutics in the treatment of chemotherapy-resistant tumors.

It has indeed been found that rutin re-establishes the sensitivity to the treatment with chemotherapeutics of resistant tumor cell lines.

The invention thus relates also to associations of rutin with substances having an anti-tumor activity, said associations being in a suitable form also for the treatment, either separate or sequential, with rutin and chemotherapeutics.

According to the invention, rutin can be used in association with all known chemotherapeutics, used either alone or in associations in chemotherapy protocols, in particular in the treatment of solid tumors. Examples of such chemotherapeutics include cyclophosphamide, 5-fluoruracyl, methotrexate, platinum complexes (cisplatin, oxaliplatin, carboplatin, etc.), taxanes, doxorubicin, epirubicin, mitoxanthrone.

According to a preferred aspect, the invention relates to compositions containing an association of alkaloids from Berberidaceae and Papavaeraceae, lignans from Asteraceae, and rutin.

In particular, the compositions of the invention preferably contain as lignans arctigenin and arctiin, as alkaloids berberine, berbamine, sanguinarine, chelerythrine, rutin.

The compositions of the invention are particularly useful for preventing and/or treating neoplasias and for preventing/suppressing chemoresistance to antiblastics and/or radioresistance to radiotherapy.

Plants belonging to the family of Asteraceae (*Arctium lappa, Cnicus benedictus* e *Saussurea medusa* or other species of *Saussurea*) are characterized in that they contain arctigenin and arctiin, which molecules are already known for their anti-tumor action. The use of extracts of *Arctium lappa* in the therapy and prophylaxis of cancer is described for instance in CN 1560265. The use of *Saussurea* as an anti-tumor agent is described for instance in patent application WO 2006 032380. The anti-tumor activity of lignans extracts from shoots of *Saussurea medusa* has been described in *Cancer Letters*, New York, USA, vol. 158, No. 1, 2000.1.1, pages 53-59.

Plants belonging to the family of Berberidaceae (*Berberis vulgaris, Berberis aristata*, other species of *Berberis*, and *Mahonia aquifolium*) contain active substances such as berberine and berbamine. The first one inhibits chemoresistance and radioresistance, neoangiogenesis and telomerase; it has an anti-hypercholesterolemic, anti-diabetic and cardioprotective effect. However, it has the serious drawback of potentially inducing MDR (multidrug resistance). In order to contrast this undesired effect, it is possible to use berbamine which, beyond the cardioprotective effect already mentioned for berberine, shows a specific anti-tumor effect towards MDR and an anti-arrhythmic effect. See also the work published in *Alternative and Complementary Therapies*, Mary and Ann Liebert, Larchmont, N.Y., USA. Vol. 8, No. 6, 2002 Dec. 1, pages 336-340, summarizing knowledge about the use of plants containing berbamine for contrasting MDR. The cytotoxic effect of the fruit of *Berberis vulgaris* has been described in *Int. J. Cancer Res*. (Vol 2, No. 1, 2006, pages 1-9).

Plants belonging to the family of Papaveraceae (*Eschscholzia californica, Macleaya cordata* or *Bocconia frutescens*) contain chelerythrine and sanguinarine. Chelerythrine has an inhibitory effect on the production of TNF-alpha: this effect, although unsuitable for tumors at an initial stage, is nevertheless precious at a pre-terminal and terminal stage since it suppresses anorexia, cachexia and hyperalgesia that are typical of pre-terminal and terminal stage oncological patients. Moreover, chelerythrine reduces mitochondrial respiration which is known to be already poor in mitochondria of tumor cells. Sanguinarine inhibits both NF-kB and AP-1 [*Biochem. Pharmacol*. 2004 Sep. 15; 68(6): 1101-11]: both are usually quiescent factors that are activated as a result of the exposition to anti-tumor antiblastics or to ionizing radiation. The preparation of anti-tumor extracts of *Macleaya cordata* or *Chelidonium majus* (a plant that is not admitted as a food supplement) containing chelerythrine is described in CN 1470513. The anti-tumor activity of benzophenanthridine alkaloids such as chelerythrine and sanguinarine, and of protoberberine alkaloids such as berberine is also described in *Planta Medica*, Vol. 69(2), 2003.2.1, pages 97-108.

The invention therefore relates to compositions containing arctigenin, arctiin, berberine, berbamine, sanguinarine, chelerythrine and rutin in mixture with suitable excipients.

The active ingredients can be present in a substantially pure and isolated form or in the form of at least three different extracts of plants, one belonging to the family of Asteraceae, one belonging to the family of Berberidaceae, one belonging to the family of Papaveraceae, apart from rutin.

Plants belonging to the family of Asteraceae are preferably *Arctium lappa, Cnicus benedictus* and *Saussurea medusa*.

Plants belonging to the family of Berberidaceae are preferably *Berberis vulgaris, Berberis aristata* and *Mahonia aquifolium*.

Plants belonging to the family of Papaveraceae are preferably selected from the group comprising *Eschscholzia californica, Macleaya cordata* or *Bocconia frutescens*.

According to a preferred aspect, the compositions of the invention will contain, apart from rutin, extracts derived from:
a) *Arctium lappa*, in particular from the seeds thereof;
b) *Berberis vulgaris;*
c) *Eschscholzia californica*.

According to a preferred aspect, extracts derived from each plant belonging to the different families will be present in a proportion of 20% to 60%.

The daily doses of the compounds isolated from the extracts will usually be included in the following ranges:
arctigenin and arctiin: 0.1-1.0 g/die
berberine and berbamine: 0.1-1.0 g/die
sanguinarine and chelerythrine: 0.01-0.250 g/die, preferably 0.020-0.150 g/die
rutin: 0.1-0.2 g/die.

According to the invention, the extracts of plants used can be in the form of oily macerate, alcoholic extract, dry extract (obtained by extraction with ethanol or with methanol or with supercritical $CO_2$), fluid extract or mother tincture.

The compositions of the invention can be used as food supplements, suitably formulated for oral administration, and will be prepared according to conventional methods well known in the pharmaceutical field, such as those described in "Remington's Pharmaceutical Handbook", Mack Publishing Co., N.Y., USA, using excipients, diluents, filling agents, anti-caking agents acceptable for their final use. Examples of formulations of food supplements will be soft capsules (sealed, liquid-containing capsules) or semi-rigid or rigid capsules (with a two-part coating, containing powder or granules), pastilles, tablets, waffles, granulates, single-dose powder bags, syrups and vialoids.

The invention further relates to an association of arctigenin, arctiin, berberine, berbamine, sanguinarine, chelerythrine and rutin for preparing compositions for the treatment of neoplasias and for preventing/suppressing chemoresistance to antiblastics and/or radioresistance to radiotherapy.

The activity of the association of rutin with synthetic chemotherapeutics (cyclophosphamide) and of the association of rutin with arctigenin, arctiin, berberine, berbamine, sanguinarine, chelerythrine (referred to with the term "extracts" in the tables), was studied on resistant cell lines of adenocarcinomas and carcinomas compared with chemosensitive tumor cell lines and with line cells.

In particular, chemoresistant human tumor cells MDA-MB-231 (breast adenocarcinoma), ECV-304 (bladder carcinoma), HuH-7 (hepatocellular carcinoma) and HTB-43 (squamous cell carcinoma of the pharynx), chemosensitive tumor cells MCF-7 (breast adenocarcinoma) and non-tumor healthy human mammal fibroblasts (HMF) have been used.

The results, shown in Tables 1-3, demonstrate a directly proportional, though not linear relation between the resistance of tumor cells to the chemotherapeutic agent and the effectiveness of the chemotherapeutic agent associated to the extract and/or to rutin.

TABLE 1

| Treatment | Cell viability (%) | | |
|---|---|---|---|
| | MDA-MB-231 | MCF-7 | HMF |
| Control | 100 | 100 | 100 |
| Cyclophosphamide 1300 ng/ml | 89 | 8.6 | 42 |
| Cyclophosphamide 1000 ng/ml | 93 | 7.5 | 48 |
| Cyclophosphamide 850 ng/ml | 96 | 6.9 | 54 |
| Extracts 850 ng/ml | 94 | 5 | 82 |
| Extracts 650 ng/ml | 100 | 8 | 84 |
| Extracts 450 ng/ml | 100 | 12 | 92 |
| Rutin 100 μM | 51 | 4 | 86 |
| Rutin 50 μM | 58 | 5 | 88 |
| Rutin 20 μM | 66 | 8 | 92 |

TABLE 2

| Treatment | Cell viability (%) MDA-MB-231 |
|---|---|
| Extracts 650 ng/ml + Cyclophosphamide 850 ng/ml | 58 |
| Rutin 50 μM + Cyclophosphamide 850 ng/ml | 11 |
| Extracts 650 ng/ml + Rutin 50 μM | 16 |
| Extracts 650 ng/ml + Rutin 50 μM + Cyclophosphamide 850 ng/ml | 3 |

TABLE 3

| Treatment | Cell viability (%) | | |
|---|---|---|---|
| | ECV-304 | HuH-7 | HTB-43 |
| Control | 100 | 100 | 100 |
| Cyclophosphamide 850 ng/ml | 70 | 58 | 36 |
| Extracts 650 ng/ml | 24 | 74 | 24 |
| Rutin 50 μM + Cyclophosphamide 850 ng/ml | 17 | 46 | 21 |
| Extracts 650 ng/ml + Rutin 50 μM + Cyclophosphamide 850 ng/ml | 12 | 32 | 12 |

The following Table 4 shows data obtained on MDA-MB-231 cells with quercetin, i.e. rutin aglycone, alone or in association with cyclophosphamide. The absence of synergic effects appears quite evident, differently from the results obtained with rutin.

TABLE 4

| Treatment | Cell viability (%) MDA-MB-231 |
|---|---|
| Quercetin 100 μM | 76 |
| Quercetin 50 μM | 81 |
| Quercetin 20 μM | 91 |
| Quercetin 100 μM + Cyclophosphamide 850 ng/ml | 62 |
| Quercetin 50 μM + Cyclophosphamide 850 ng/ml | 66 |
| Quercetin 20 μM + Cyclophosphamide 850 ng/ml | 79 |

Examples of preparation of the extracts used in the invention as well as examples of compositions of the invention are disclosed below.

Example 1—Preparation of an Alcoholic Extract from Fresh Plants 530 grams consisting of the three plants together (each in a proportion of 20% to 60%) are placed in 1100 ml of an ethanol/water mixture (40% to 90% ethanol) and ground in a mixer. The whole is left to "rest" for a period of 4 to 8 days, taking care that ground plants are submerged in the solution. At the end of this period the liquid part is removed, the vegetable part is pressed, the liquids are gathered and then filtered. The extract thus obtained has an intense green-brownish color.

Example 2—Preparation of an Alcoholic Extract from Dry Plants

An amount of dry plants of 370 to 450 grams is used for 1200 ml of hydroalcoholic solution (40% to 90% ethanol). The whole is left to "rest" for about two weeks. At the end of the impregnation/dyeing of the solvent, the liquid part is removed, the vegetable part is pressed, the liquids are gathered and then filtered.

The invention claimed is:

1. A composition comprising arctigenin, arctiin, berberine, berbamine, sanguinarine, chelerythrine, and rutin, in a mixture with suitable excipients.

2. The composition according to claim 1, wherein the arctigenin, arctiin, berberine, berbamine, sanguinarine, chelerythrine are in form of plant extracts derived from:
   a plant belonging to the family of Asteraceae selected from *Arctium lappa, Cnicus benedictus* and *Saussurea medusa*;
   a plant belonging to the family of Berberidaceae selected from *Berberis vulgaris, Berberis aristata* and *Mahonia aquifolium*; and
   a plant belonging to the family of Papaveraceae selected from *Eschscholzia californica, Macleaya cordata* or *Bocconia frutescens*.

3. The composition according to claim 2, wherein the arctigenin, arctiin, berberine, berbamine, sanguinarine, chelerythrine are in form of plant extracts derived from:
   *Arctium lappa*;
   *Berberis vulgaris*; and
   *Eschscholzia californica*.

4. A method of treating a subject, the method comprising:
   administering to the subject a composition comprising arctigenin, arctiin, berberine, berbamine, sanguinarine, chelerythrine and rutin compounds in an effective amount to treat neoplasies and prevent and/or suppress chemoresistance to antiblastics and/or radioresistance to radiotherapy in the subject.

5. A method of treating chemoresistant tumors in a subject, the method comprising:
   administering to the subject an effective amount of rutin in association with chemotherapeutics and/or with arctigenin, arctiin, berberine, berbamine, sanguinarine, and chelerythrine compounds,
   wherein the arctigenin, arctiin, berberine, berbamine, sanguinarine, chelerythrine are in form of plant extracts.

6. The composition of claim 2, wherein each plant extract is in a proportion between 20% and 60%.

7. The composition of claim 2, wherein the form of plant extracts is oily macerate, alcoholic extract, dry extract, fluid extract or mother tincture.

8. The method of claim 4, wherein the arctigenin, arctiin, berberine, berbamine, sanguinarine, chelerythrine are in form of plant extracts.

* * * * *